United States Patent [19]

Rankin

[11] Patent Number: 4,954,676
[45] Date of Patent: Sep. 4, 1990

[54] ELECTRICALLY HEATED STUFFED TOY WITH CONCENTRATED HEAT DISSIPATION

[75] Inventor: Martin D. Rankin, Roleystone, Australia

[73] Assignee: Axti Pty Ltd., Mt. Hawthorn, Australia

[21] Appl. No.: 144,561

[22] Filed: Jan. 14, 1988

[30] Foreign Application Priority Data

Jan. 15, 1987 [AU] Australia .............................. PH9886

[51] Int. Cl.⁵ .......................... H05B 3/00; A61F 7/08
[52] U.S. Cl. .................................... 219/200; 128/399; 219/528; 219/540; 383/901; 446/484
[58] Field of Search ............... 219/200, 201, 528, 529, 219/535, 540; 128/399; 383/901; 446/484, 485, 369–373, 73–76

[56] References Cited

U.S. PATENT DOCUMENTS

| | | | |
|---|---|---|---|
| 1,439,094 | 12/1922 | Gingras | 219/529 |
| 1,837,117 | 12/1931 | Dunbar | 219/528 X |
| 1,896,663 | 2/1933 | Collins | 219/529 X |
| 2,215,042 | 9/1940 | Howard et al. | 219/529 |
| 2,287,320 | 6/1942 | Mitchell | 219/529 |
| 2,647,195 | 7/1953 | Broyles | 219/200 X |
| 3,103,219 | 9/1963 | Chadner | 219/528 X |
| 3,202,801 | 8/1965 | Saluri | 219/528 |
| 3,780,262 | 12/1973 | Rudd | 219/528 X |
| 4,694,829 | 9/1987 | Frye | 128/399 |

FOREIGN PATENT DOCUMENTS

| | | | |
|---|---|---|---|
| 2403865 | 8/1975 | Fed. Rep. of Germany | 219/200 |
| 58-60157 | 9/1983 | Japan | 219/200 |
| 8607662 | 12/1986 | PCT Int'l Appl. | |

*Primary Examiner*—Anthony Bartis
*Attorney, Agent, or Firm*—Harness, Dickey & Pierce

[57] ABSTRACT

An electrically heated soft toy for transmitting warmth to a person hugging the toy includes an outer casing filled with a soft stuffing material enclosing a battery powered electrically heated heat storage mass disposed in a cavity in the stuffing material and surrounded by a resiliently flexible mass of fibrous heat transfer material, such as a mass of tangled copper wires, having a greater thermal conductivity than the stuffing material. The stuffing material surrounds the fibrous heat transfer material except for a portion of the fibrous material which is in direct engagement with a selected portion of the outer casing so that heat is concentrated at a specific region on the exterior surface of the soft toy, which region may be reinforced by a flexible panel of durable wear resistant material, thereby making the transfer of heat to the person using the toy more effective.

17 Claims, 6 Drawing Sheets

ELECTRICALLY HEATED STUFFED TOY WITH CONCENTRATED HEAT DISSIPATION

BACKGROUND OF THE INVENTION

This invention relates to a heating means for providing warmth to a human body or to an object such as a bed.

The heating means has been devised particularly, but not solely, to take the form of a soft toy, such as a stuffed animal or doll, which is capable of transmitting warmth to the a person cuddling or otherwise in close contact with the soft toy. The heating means may, however, take other forms such as a pillow, a backrest or a footrest.

Many people and in particular children find enjoyment in, and comfort from, soft toys because of the cuddly nature. It is believed that the enjoyment in, and comfort from, a soft toy would be enhanced if the toy provided warmth to a person holding it.

In International Patent Application No. PCT/GB86/00361, there is disclosed an article (which may take the form of a teddy bear) for transmitting warmth to a person hugging the article or to a bed in which the article is placed. The article comprises a body portion stuffed with material which is flexible and which has heat transfer characteristics. A heat source is disposed within and surrounded by the stuffing material. With this arrangement, it is intended that heat generated by the heat source is transmitted to the exterior surface of the article by virtue of the heat transfer properties of the stuffing material. The intended effect of this is that warmth would be transmitted to a person hugging the article or to a bed in which the article is placed.

It is, however, believed that the article disclosed in the abovementioned international application has a deficiency in that heat is transferred through the stuffing material in all directions and so only a marginal increase in the surface temperature of the article would be attained before heat stored in the heat source becomes so depleted as to no longer be effective.

It is an object of the present invention to provide a novel and useful heating means in which the abovementioned deficiency has been eliminated or at least reduced.

SUMMARY OF THE INVENTION

In one form the invention resides in a heating means comprising a soft body containing stuffing material, a heat source within the stuffing material and spaced from the exterior of the body, and a flexible heat transfer means between the heat source and a portion of said exterior surface, the heat transfer means being of higher thermal conductivity than the stuffing material.

With this arrangement, heat is concentrated at said portion of the exterior surface of the body and consequently that portion becomes perceptibly warmer than other portions of the surface at which there is no concentration of heat. Thus, more benefit is derived from the heat in the sense that the heat is perceptible to a user because of its concentrated nature.

Because the heat transfer means is flexible, it maintains the soft characteristics of the body.

Preferably, said heat transfer means is resiliently flexible. The heat transfer means may comprise a bundle of heat conductive fibre material such as a tangled mass of copper wire.

Preferably, the heat source comprises a mass of heat storing material and means for heating said mass. With this arrangement, the mass can store heat generated and dissipate it slowly.

Preferably, the mass of heat storing material presents a broad face and said heat transfer means is in contact with said broad face. In this connection, the mass of heat storing material may be in the general form of a plate with one face of the plate defining said broad face.

Preferably, the heating means comprises an electric heating means. The electric heating means may be energised from a mains supply or other power source remote from the soft body. Additionally, or alternatively, the electric heating means may be energised from a power source housed on or within the soft body.

The electric heating means may generate heat by means of an electrical resistance device or a transistor heating device.

The electric heating means may include a control means to protect the heating circuit against overheating.

Where the heating means is in the form of a soft toy having a trunk, said portion to which heat is concentrated is preferably at the front of the trunk portion. This facilitates transmission of warmth to a person who hugs the toy in the usual way.

BRIEF DESCRIPTION OF THE DRAWINGS

The invention will be better understood by reference to the following description of one specific embodiment thereof as shown in the accompanying drawings in which.

DETAILED DESCRIPTION OF THE PREFERRED EMBODIMENTS

The embodiment is directed to a heating means in the form of a soft toy and more particularly a teddy bear.

Figure 1:
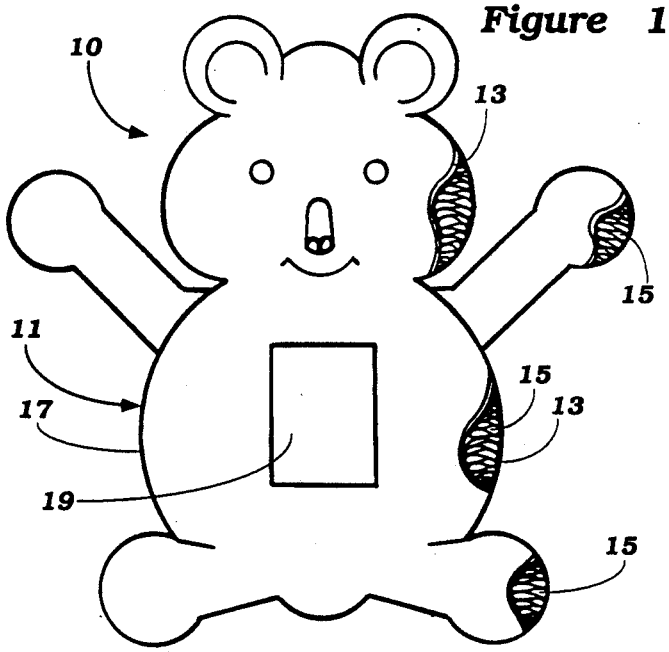
FIG. 1 is a front view of an article according to the embodiment with portions of the article broken away to reveal stuffing material contained within the body of the article.
Figure 2:
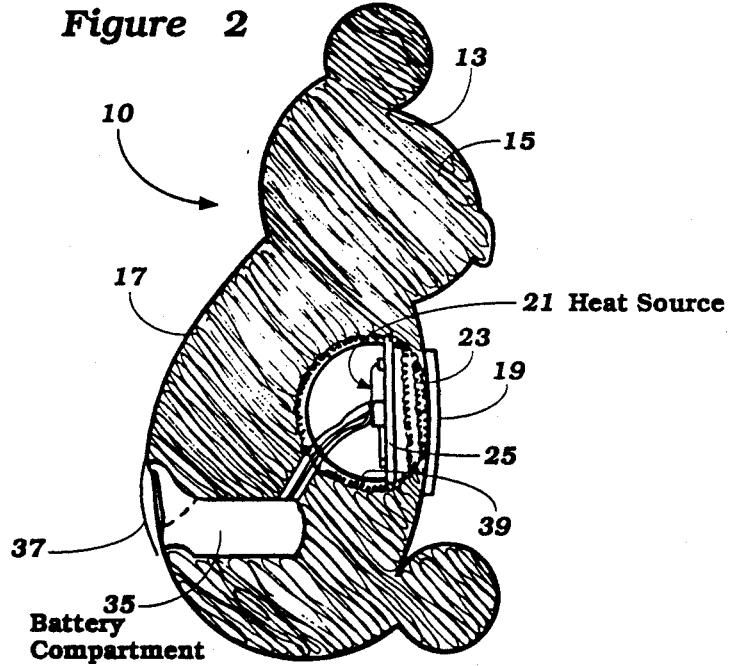
FIG. 2 is a sectional side view of the embodiment.
Figure 3:
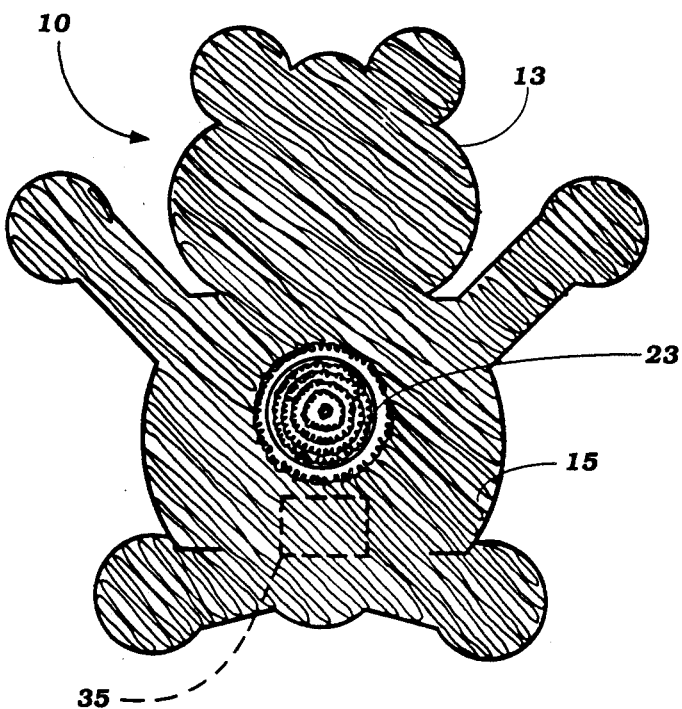
FIG. 3 is a sectional front view of the embodiment.

Referring to FIGS. 1 and 3, the teddy bear 10 comprises a soft body 11 in the form of a flexible outer casing 13 partly stuffed with flexible stuffing material 15 of conventional kind. The front of the trunk portion 17 of the teddy bear is reinforced with a flexible panel 19 of durable material.

A heat source 21 is provided within a cavity formed by the flexible stuffing material 15 and the front of the trunk portion 17 of the teddy bear and is spaced from the outer casing 13 and is positioned at the base of this cavity.

A heat transfer means 23 of flexible construction has a first portion that is in direct engagement with the heat source 21 and which extends between the heat source 21 and the portion of the casing 13 covered by the panel 19 on the trunk portion of the teddy bear. The heat transfer means 23 has a second portion in direct engagement with the panel 19 and the remaining portion of the flexible heat transfer means 23 is surrounded by the stuffing material and supported thereby.

The heat source 21 comprises a mass of heat storing material 25 and an electric heating means 27 for heating the mass of heat storing material. In this embodiment, the mass of heat storing material 25 is in the form of a generally circular plate of aluminium alloy. The heat transfer means 23 is located adjacent the front face 29 of the circular plate 25 and the electric heating means 27 is provided on the rear face 31 of the circular plate.

The electric heating means 27 includes an electric circuit 32 incorporating a transistor heating device 33 which is mounted on the rear face of the circular plate 25. The electric circuit also includes a power source in the form of a battery (not shown) located in a battery compartment 35 provided in the teddy bear. Access to the battery compartment 35 is provided by a releasable flap 37. A switch (not shown) is provided to enable the power source to energise the electrical circuit.

The battery is preferably rechargable by mains supply. The electrical circuit 32 is also designed to enable energisation from a mains supply through a transformer.

The electric circuit is also provided with a control means to protect the circuit against overheating.

A casing 39 in the form of a dome constructed of plastic material, is mounted onto the rear face 31 of the circular plate 25 to house the transistor heating device 33 and various other components of the electric circuit. The casing is mounted on the plate 25 by means of mounting pins 40 on the casing which locate in corresponding mounting holes 42 formed in the plate. The outer surface of the casing is provided with outwardly extending projections 41 which penetrate stuffing material 15 contained within the casing 13 of the teddy bear so as to locate the heat source and electrical heating circuit in position within the teddy bear.

Figure 4:
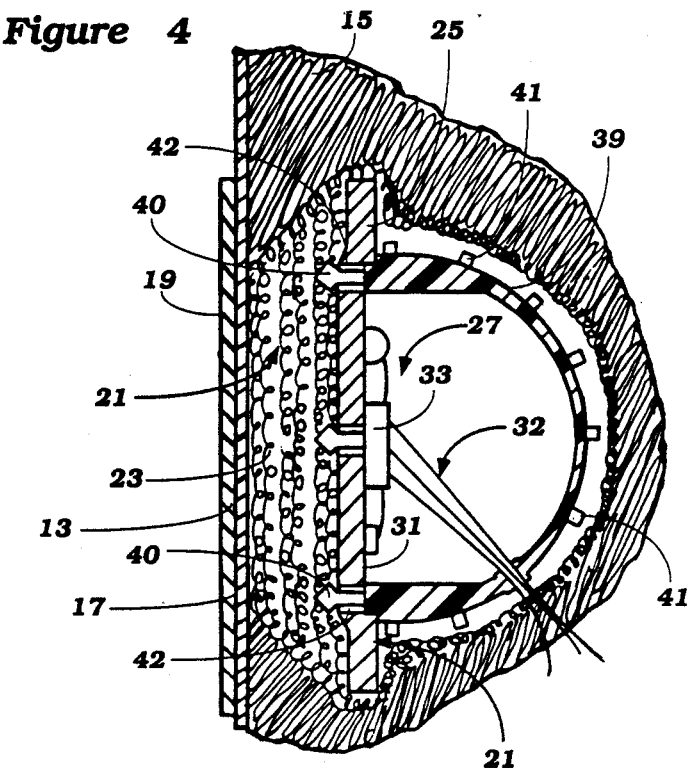
FIG. 4 is a schematic sectional side view of a heat store and heat transfer means which form part of the embodiment and shows its relationship to the stuffing material and outer casing.
Figure 5:
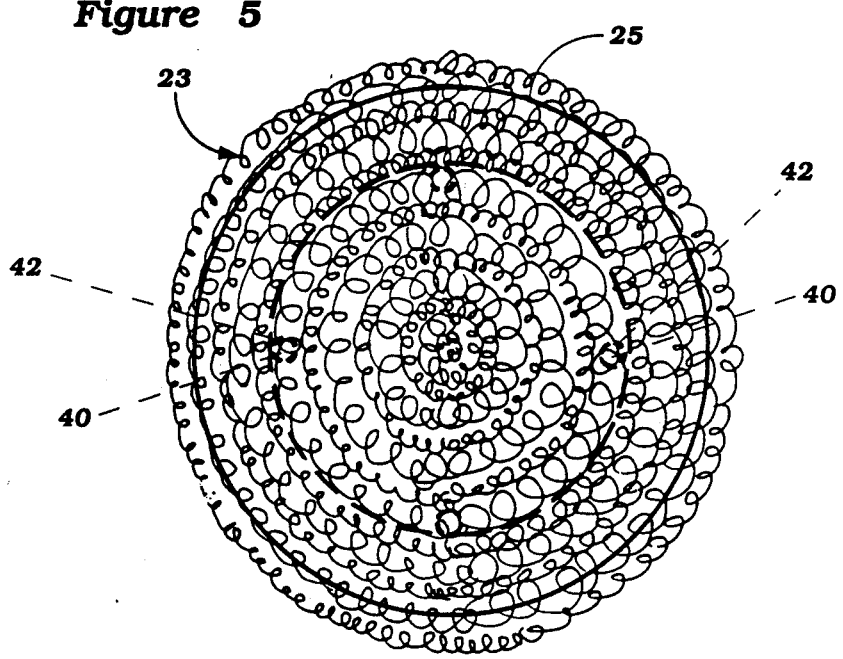
FIG. 5 is a front view of the heat store and heat transfer means of FIG. 4.
Figure 6:
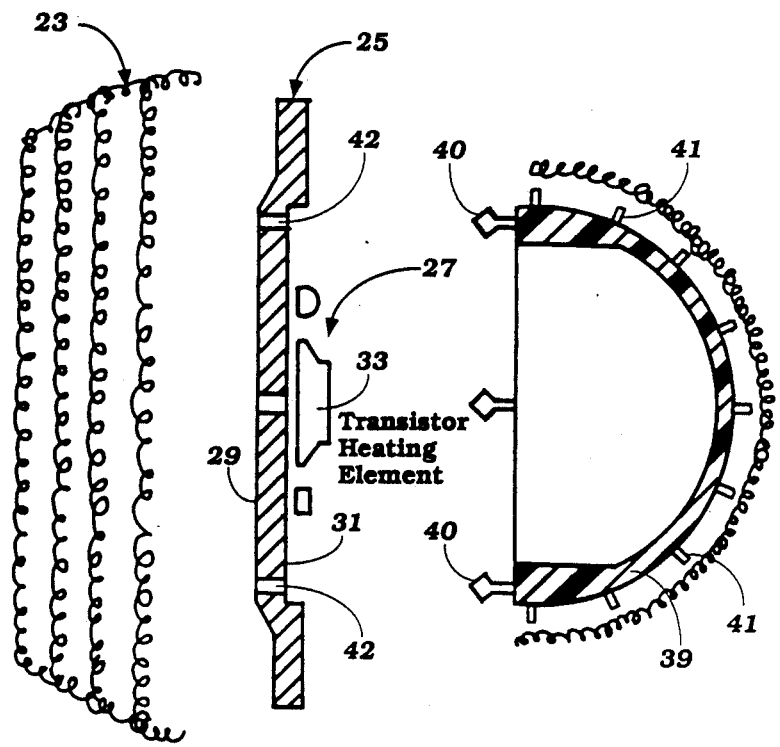
FIG. 6 is an exploded cross-sectional view showing parts of the heat store and heat transfer means of FIG. 4.
Figure 7:
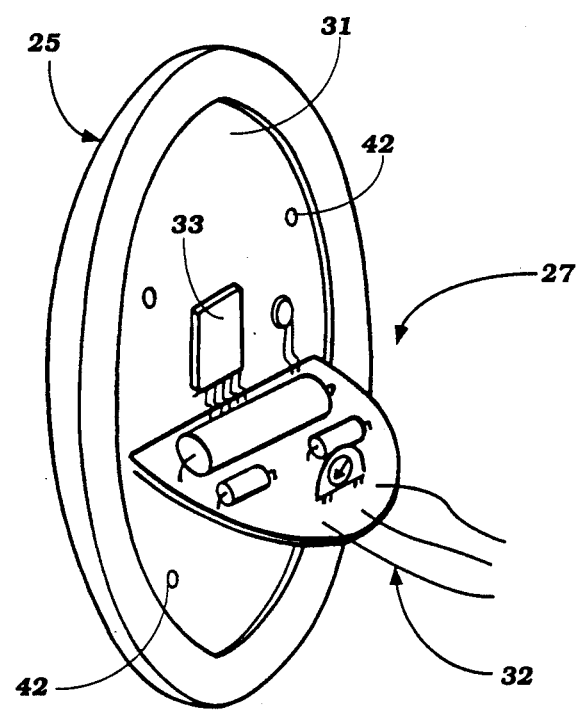
FIG. 7 is a perspective view of the heat store of FIG. 4.

The heat transfer means 23 is in the form of a tangled mass of copper wire which is secured to the circular plate 25 and casing 39 by wrapping part of the wire around the casing, as best seen in FIG. 4. The copper wire has a considerably higher thermal conductivity value than the stuffing material 15. Therefore, the tangled mass of copper wire provides a heat transfer zone between the front face 29 of the circular plate 25 and the panel 19 on the exterior surface of the teddy bear.

The flexible nature of the heat transfer means 23 maintains the soft characteristics of the body of the teddy bear.

To heat the teddy bear in preparation for use, the electrical circuit 32 is energised to heat the circular plate 25. Energisation of the electrical circuit may be by way of electrical energy from the battery contained within the battery compartment 35 or from electrical energy derived from a remote power source such as a main supply. In the latter case, for safety purposes the electrical circuit 32 is disconnected from the mains supply before the teddy bear is put into use. The circular plate 25 stores heat generated by the electric heating means and subsequently dissipates the heat predominantly through the heat transfer means 23 to the panel 19 on the exterior surface of the teddy bear. In this way, heat is concentrated at the panel 19 on the exterior surface of the teddy bear and thus the panel attains a perceptably higher temperature than the remainder of the exterior surface of the teddy bear. Consequently, warmth will be transmitted to a person or object in contact with the panel 19 of the teddy bear. In the case of a person hugging the teddy bear, the feeling of warmth and enjoyment received by that person should be enhanced by the warmth transmitted to the person.

Figure 8:
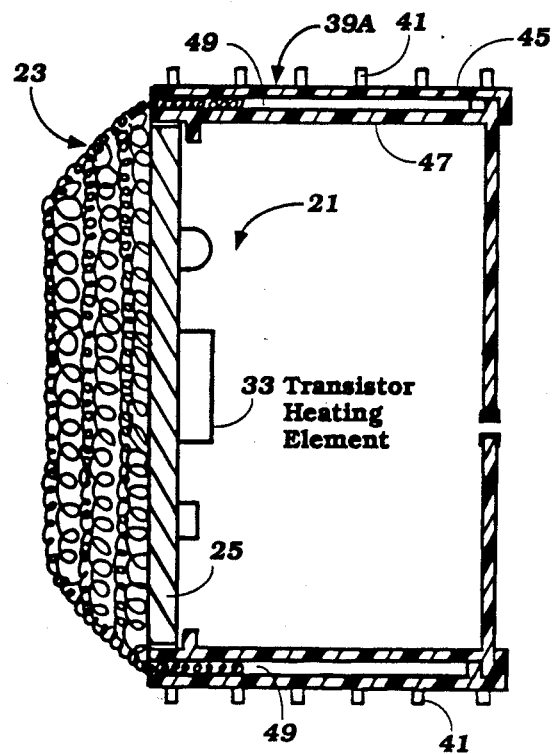
FIG. 8 is a schematic sectional side view of another form of heat store and heat transfer means for use in the embodiment.
Figure 9:
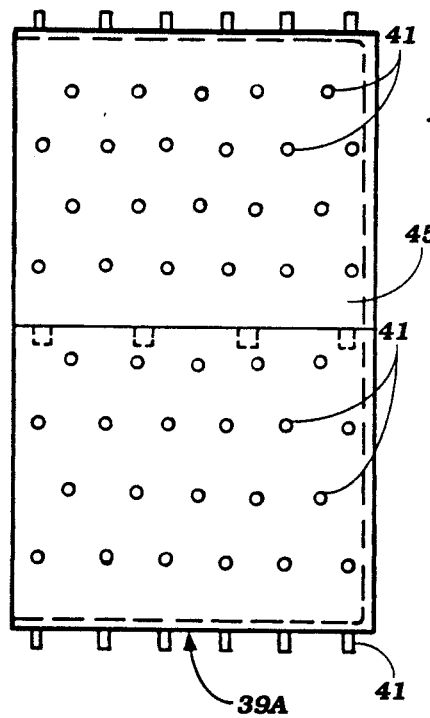
FIG. 9 is a schematic side view of part of the heat store and heat transfer means shown in FIG. 8.

FIGS. 8 and 9 of the drawings show another construction for the casing attached to the circular plate 25 of heat storing material and an alternative manner for attaching the mass of copper wire 23 to the casing. In this alternative construction, the casing 39A is formed in two generally cylindrical parts 45 and 47 which fit together and co-operate to secure the mass of copper wire to the edge of the casing surrounding the circular plate 25. More particularly, the two parts 45 and 47 co-operate to define a space 49 which surrounds the circular plate 25 and into which part of the tangled mass of copper wire is received and clampingly retained. The outer surface of casing part 45 is provided with projections 41 for penetrating stuffing material within the teddy bear.

From the foregoing it is evident that the soft toy according to the embodiment retains its generally soft characteristics notwithstanding the presence of the heat source and heat transfer means within the body of the toy. This is because of the flexible nature of the heat transfer means. Moreover, it is evident that heat is concentrated at a specific region of the exterior surface of the toy thereby to ensure that the surface temperature at that region is significantly higher than the surface temperature at other parts of the soft toy. Because of this, a person hugging the soft toy can readily feel warmth transmitted by the soft toy.

It should be appreciated that the scope of the invention is not limited to the scope of the embodiment described. In particular, it should be appreciated that the heating means according to the invention may have applications in articles other than soft toys; such articles may include pillows, backrests and footrests.

I claim:

1. A heating means to be used by a person and held against the person's body for warmth comprising a soft flexible body having a flexible outer casing, a stuffing material substantially filling said outer casing, said outer casing and said stuffing material defining a cavity adjacent a portion of said outer body and extending into and surrounded by said stuffing material, a heat source within said outer casing and supported within and by said stuffing material at a base of said cavity spaced from said outer casing portion, and a flexible heat transfer means within said cavity, said flexible heat transfer means having a first portion engaged with said heat source and a spaced portion engaged with said portion of said outer casing of said body for transferring heat thereto from said heat source, the remaining portion of said heat transfer means not engaged with said heat source or with said outer casing portion being surrounded by said stuffing material, said heat transfer means being of higher thermal conductivity than said stuffing material.

2. A heating means according to claim 1 wherein the heat transfer means is resiliently flexible.

3. A heating means according to claim 2 wherein the heat transfer means comprises a bundle of heat conductive fibrous materials.

4. A heating means according to claim 3 wherein the heat conductive fiberous material comprises copper wire.

5. A heating means according to claim 1 wherein the heat source comprises a mass of heat storing material.

6. A heating means according to claim 5 wherein the mass of heat storing material has a substantial surface area in contact with the first portion of the heat transfer means.

7. A heating means according to claim 6 wherein said heat storing material is in the general form of a plate and wherein one of the faces of said plate defines the substantial surface area.

8. A heating means according to claim 5 further including means contained within the soft body for heating the mass of heat storing material.

9. A heating means according to claim 8 wherein the means for heating said mass comprises an electric heating means.

10. A heating means according to claim 9 wherein said electric heating means includes an electric heating device mounted on the mass of heat storing material.

11. A heating means according to claim 10 wherein the mass of heat storing material is in the form of a plate with one side of the plate being in contact with the first portion of the heat transfer means and the other side of said plate being in contact with said electric heating device.

12. A heating means according to claim 1 wherein the soft body is in the form of a soft toy.

13. A heating means according to claim 12 wherein the soft toy body is in the form of an animal.

14. A heating means according to claim 13 wherein the heat source and the flexible heat transfer means is in the trunk of the animal and is in proximity to a portion of the outer surface of said outer housing that would be in contact with a human body when the human hugs the animal.

15. A heating means according to claim 14 wherein the outer surface of said portion of the body outer casing engaged with the second portion of the heat transfer means is formed from a more wear resistant surface than the remaining portion of the body outer casing.

16. A beating means according to claim 15 wherein the flexible hear transfer means is in direct heat exchanging relationship with the more wear resistant portion of the body outer casing and wherein the heat source comprises a mass of heat storing material having a substantial surface area in contact with the first portion of said flexible transfer means and an electric heating element in contact with said mass.

17. A heating means according to claim 16 further including means contained within the body for activating the electrical heating element.

* * * * *